United States Patent
Liska et al.

(10) Patent No.: US 6,346,090 B1
(45) Date of Patent: Feb. 12, 2002

(54) MICRODIALYSIS CATHETER FOR INSERTION INTO A BLOOD VESSEL

(76) Inventors: Jan Liska, Sibyllegatan 53, S-114 43 Stockholm; Anders Franco-Cereceda, Rörstrandsgatan 4, S-113 40 Stockholm, both of (SE)

( * ) Notice: Subject to any disclaimer, the term of this patent is extended or adjusted under 35 U.S.C. 154(b) by 0 days.

(21) Appl. No.: 09/359,312

(22) Filed: Jul. 23, 1999

(51) Int. Cl.[7] ................................................. A61M 1/00
(52) U.S. Cl. ......................................... 604/29; 604/264
(58) Field of Search .............................. 604/29, 27, 35, 604/264, 523, 43

(56) References Cited

U.S. PATENT DOCUMENTS

| 4,265,249 A | 5/1981 | Schindler et al. |
| 4,694,832 A | 9/1987 | Ungerstedt |
| 4,707,268 A | * 11/1987 | Shah et al. |
| 4,787,883 A | * 11/1988 | Kroyer |
| 5,106,365 A | 4/1992 | Hernandez |
| 5,441,481 A | 8/1995 | Mishra et al. |

FOREIGN PATENT DOCUMENTS

DE          0166237       *  1/1986

* cited by examiner

*Primary Examiner*—Richard K. Seidel
*Assistant Examiner*—LoAn H. Thanh

(57) ABSTRACT

A catheter for insertion into a blood vessel of a living being, which includes an elongated catheter body and membrane defining a dialysis chamber; a first channel provided for delivery of dialysis liquid to the dialysis chamber and a second channel provided for the discharge of dialysis liquid from the dialysis chamber, wherein the dialysis chamber comprises a plurality of tubular members, each having an inlet end and an outlet end, all the inlet ends being connected to the first channel and all the outlet ends being connected to the second channel.

5 Claims, 2 Drawing Sheets

MICRODIALYSIS CATHETER FOR INSERTION INTO A BLOOD VESSEL

FIELD OF THE INVENTION

The present invention relates to a catheter adapted to be inserted into a blood vessel in order to perform various analyses in the body of a living being, such as in the heart, the liver, the kidney, a pulmonary artery, or, a limb.

BACKGROUND OF THE INVENTION

Microdialysis is used to monitor the interstitial fluid in various body organs with respect to local metabolic changes. The technique is also experimentally applied in humans for measurements in adipose tissue.

U.S. Pat. No. 4,694,832 discloses a dialysis probe comprising a dialysis membrane with associated ducts for achieving a perfusion fluid flow over the membrane. The single membrane is tubular and consists of a thin-walled permeable hose material referred to as a "hollow fiber" membrane. Ducts are provided for supplying and removing perfusion liquid to and from the interior of the membrane, and one of these ducts is disposed inside the hollow fiber membrane to extend to the distal end thereof. In order to protect and support the very thin membrane, the membrane is surrounded by a mounting, which is more rigid than the membrane and is preferably made as a thin-walled metal sleeve. The membrane is inserted in the mounting to be as close as possible to the wall of the sleeve. The wall of the sleeve has an opening in which a portion of the membrane surface is exposed. Although the size of this opening may vary depending on the desired size of the dialyzing surface of the membrane, it is evident that it cannot be large enough to meet all requirements for optimum dialysis, since then the protective and support properties of the sleeve would be lost.

U.S. Pat. No. 5,106,365 discloses a microdialysis probe comprising an outer sleeve containing tubes for delivering and removing dialysis products. The dialysis membrane is directly fixed to the end edge of the outer sleeve by gluing. This prior art probe is not suited for insertion in a blood vessel since the membrane constitutes the tip of the probe.

U.S. Pat. No. 5,441,481 discloses a microdialysis probe arranged to have a primary probe, e.g., an electrical probe, concentrically located within it to enable the combined microdialysis probe and primary probe to be extended as a unit through a common opening into the body of a living being. The microdialysis probe comprises a tube having a lumen therethrough for releasably mounting the primary probe, and at least one dialysis chamber. The dialysis chamber comprises a wall formed of a semi-permeable material, an inlet passageway to the chamber and an outlet passageway from the chamber.

Reference is made also to SE 9800791-7 (filing date Mar. 11, 1998) and PCT/SE99/00259 (claiming priority from SE 9800791-7 and having a filing date Feb. 24, 1999), both by the same inventors and neither published at the filing date of the present application. The prior application concerns a catheter to be inserted into and guided by a blood vessel, and it comprises an elongate catheter body, having a distal end and a proximal end. An outer essentially cylindrical surface, limiting a wall structure, encloses at least two channels including a first and a second channel for microdialysis solution, each channel having a proximal end and a distal end. The first and second channels are interconnected at a first distance from the distal end of the catheter body so that microdialysis solution can flow from one channel to the other. An opening is provided in the catheter body at a second distance from its distal end, and a microdialysis membrane is arranged in to cover the opening. A space in the catheter body formed by a portion of the first channel in connection with the opening forms a microdialysis chamber, having at least a portion of the microdialysis membrane as a part of its walls. The proximal ends of the first and second channels are connectable to external means for circulating, monitoring and/or analyzing the dialysis solution.

Although this prior microdialysis catheter represents a major step forward in the art of microdialysis, it still suffers from the main drawback of all prior art microdialysis catheters, viz. a low ratio of area to volume, i.e. the effective area of the membrane in relation to the volume of dialysis solution passing the membrane per unit of time. In order to obtain the best possible recovery, it is important that the relationships of area to volume is as high as possible.

SUMMARY OF THE INVENTION

It is an object of the present invention to provide a new catheter intended for insertion into a blood vessel for performing blood analysis, primarily by microdialysis, said catheter being provided with membrane means enabling a maximum effective area of microdialysis membrane and a minimum of volume flow of perfusion fluid (perfusate).

To achieve this object, the present invention proposes, instead of the conventional use of a continuous sheet of membrane, or, as in U.S. Pat. No. 4,694,832, the use of one single tubular membrane, the use of a plurality of tubular membranes the interiors of which together constitute the dialysis chamber. Thus, one end of each such tubular membrane is connected to a common delivery channel for perfusion fluid and the other end of each such tubular membrane is connected to a common discharge channel for perfusion fluid, thus achieving parallel flows of perfusion fluid through the membranes, whereas the exteriors of all the tubular membranes are caused to contact the blood to be analyzed. It is preferred to arrange all tubular membranes along the periphery of a cylinder, either parallel to the cylinder axis or in a helical manner.

BRIEF DESCRIPTION OF THE DRAWING

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description, wherein.

DESCRIPTION OF A PREFERRED EMBODIMENT

Figure 1:
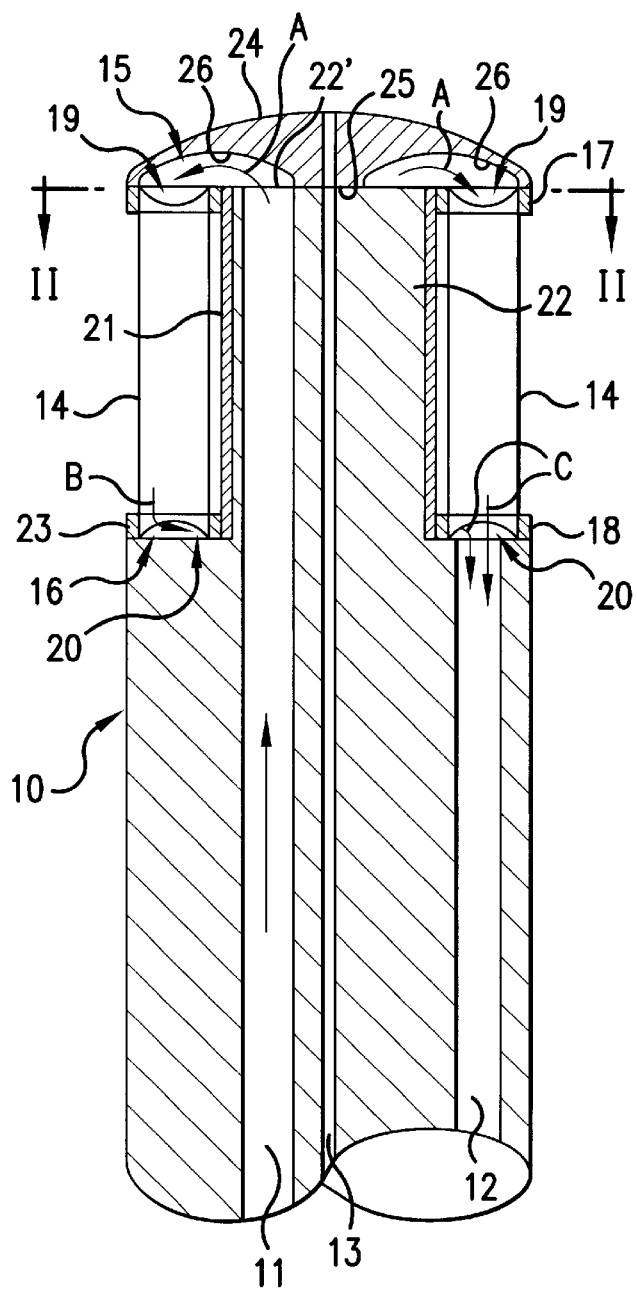
FIG. 1 is a longitudinal sectional view of the distal end of a preferred embodiment of a catheter according to the present invention.
Figure 2:
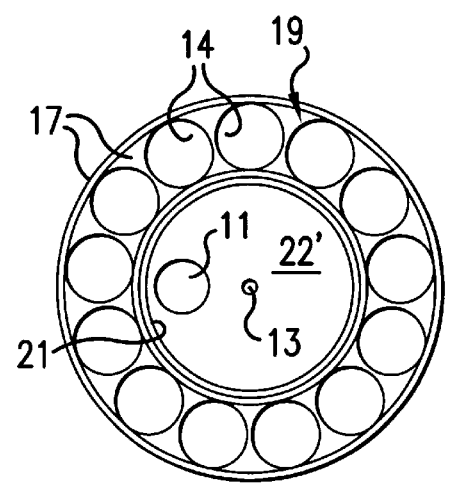
FIG. 2 is a cross-sectional end view of the catheter seen in the direction of arrows II—II in FIG. 1 and having its end cap removed.

The embodiment of the catheter shown in FIGS. 1 and 2 includes an elongate, preferably flexible catheter body 10 having an essentially cylindrical outer surface. Inside the body there are at least two channels 11, 12 for delivery and discharge, respectively, of a perfusion fluid. These channels are preferably eccentrically located as shown. It is also preferred to have a central channel 13 for a non-shown guide wire by means of which the catheter can be guided into different organs as is well known in the art of catheterization. There may also be further channels arranged through the catheter body, such as for air to inflate a balloon at the tip of the catheter, or, for one or more electrical wires connected to electrodes at the distal end of the catheter. The material of the catheter body is preferably radio opaque, and an echo crystal means is suitably provided close to the distal end thereof so as to enable identification of the catheter end by ultra sonar graphy.

As is known in the art of microdialysis, the perfusion fluid is delivered through one of the channels, e.g. channel 11, to a dialysis chamber having at least a portion of its wall defined by a semi permeable membrane. The other side of the membrane is located in the blood flow of a blood vessel so that substances contained in the blood may pass through the membrane to be brought along by the perfusion fluid and discharged through the other channel, e.g. channel 12, which is connected to suitable apparatus for performing the desired measurements.

According to the present invention there is provided a plurality of tubular membranes 14, the interiors of which together form the dialysis chamber. To achieve this, one end of each tubular membrane (here the distal end) is connected to a common delivery channel 11 for perfusion fluid and the other end of each tubular membrane (here the proximal end) is connected to a common discharge channel 12 for the perfusion fluid. There is obtained, thus, parallel flows of perfusion fluid through the membranes.

In order to provide for parallel flows, there is arranged at the distal, or inlet ends of the tubular membranes a distribution chamber 15, into which the inlet ends of all tubular membranes 14 open. The distribution chamber also communicates with the delivery channel 11. Likewise, there is provided at the proximal, or, outlet ends of the tubular membranes a collection chamber 16, into which open the outlet ends of all the tubular membranes. The collection chamber also communicates with the discharge channel 12.

It is known in the art of handling hollow fibers to embed the ends of a plurality of fibers in a hardening compound and then, after hardening, to treat the hardened compound, e.g., by machining, so as to obtain access to the interior of each fiber. The present invention takes advantage of this knowledge by embedding the ends of the fibers in a hardening compound shaped as two similar annular blocks 17, 18. The blocks are machined in their surfaces facing from each other to provide an annular recess 19, 20, respectively, constituting a part of the distribution chamber 15 and the collecting chamber 16, respectively.

The composite structure comprising the distal annular block 17, a plurality of parallel hollow fibers 14 (tubular members) and the proximal annular block 18 is arranged around the circumference of a relatively stiff supporting cylinder or sleeve 21. In its distal end, the cross section of the catheter body 10 is reduced so as to leave a straight cylindrical portion 22 coaxial to the catheter body, and having an outer diameter adapted to the inner diameter of the sleeve 21 and a height adapted to the height of the sleeve 21 and the length of the hollow fibers. The reduced cross section also provides an annular shelf 23, the plane of which is perpendicular to the axis of the catheter body 10. The discharge channel 12 opens in the shelf 23. By arranging the sleeve 21 around the cylindrical portion 22 such that the proximal block 18 rests on the shelf, communication will be established between the discharge channel and the annular recess 20 forming the collection chamber 16.

At the distal end of the catheter body there is arranged a cap 24 having an outer diameter adapted to the outer diameter of the distal annular block 17 and contacting this block in a fluid tight manner around its circumference. In the contact surface 25 of the cap there is provided an annular recess 26 having a radial extension sufficient to cover the annular recess 19 of the distal block 17 as well as the delivery channel 11 opening in the end face 22' of the cylindrical portion 22 radially inwardly of the recess 19. The annular recess 26 completes the annular recess 19 to form the distribution chamber 15 in which opens the delivery channel 11, thus enabling fluid from the delivery channel 11 to enter all the tubular membranes 14 distributed 360° around the catheter as indicated by curved arrows A in FIG. 1. Having entered the tubular membranes 14, the fluid flows along the interior of each tubular membrane to collect and bring along substances having entered from the outside through the membrane walls. When reaching the proximal end of the tubular membranes, the fluid enters the collecting channel 16 (arrow B) in which opens the discharge channel 12, and the fluid is eventually directed into this channel (arrows C) and along it for further analysis as is well known in the art.

The tubular membranes 14 may contact each other, in which case an effective membrane area is provided that is substantially larger than the area of a single sheet-shaped cylindrical membrane being tangent to the outer circumference of each tubular membrane 14. It is preferred, however, to have a small spacing between adjacent tubular membranes as shown in FIG. 2, and a small clearance between each membrane and the sleeve 21, as shown in FIG. 1, thereby enabling blood to flow in between adjacent membranes and around them to provide 360° effective membranes.

Figure 3:
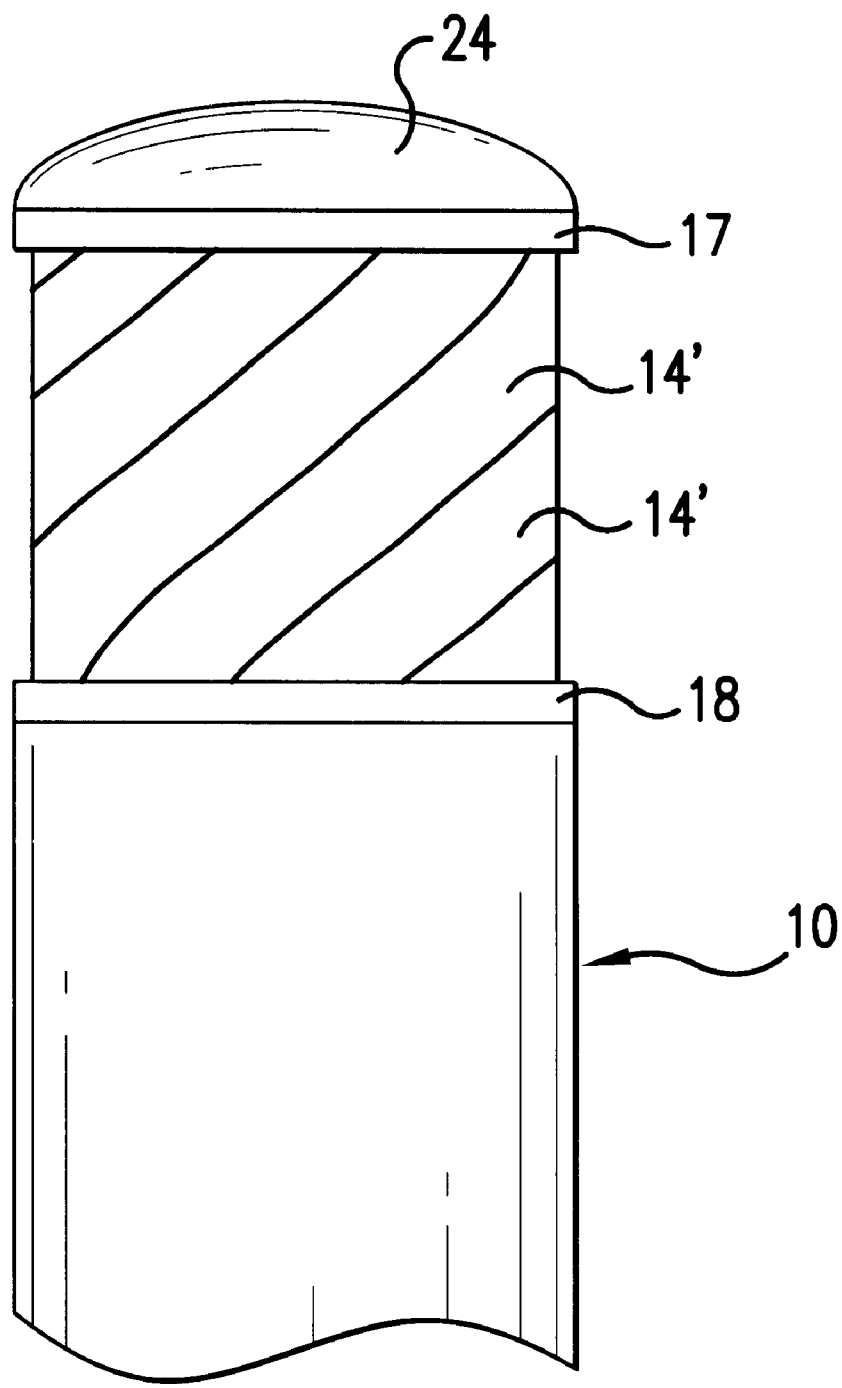
FIG. 3 is a side view of the tubular membranes arranged in a helical configuration.

As an alternative to the embodiment described in FIG. 1 having the tubular membranes parallel to the axis of the sleeve 21, it is possible to arrange each membrane inclined relative to a plane containing said axis, such that the complete dialysis chamber obtains a helical shape as shown in FIG. 3. Thereby, each tubular membrane 14' can be made longer while maintaining the height of the sleeve 21. The sectional appearance of this embodiment would be similar to that of FIG. 1.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A microdialysis catheter for insertion into a blood vessel of a living being, comprising:
    an elongate catheter body having first channel means for delivery of dialysis liquid and second channel means for discharge of dialysis liquid, a portion of said catheter body having a reduced diameter forming a straight cylindrical portion;
    a relatively stiff supporting sleeve arranged around said cylindrical portion and having an outer circumference;
    dialysis chamber means defined by a plurality of tubular membrane members arranged in close relation to one another in one layer about said outer circumference of said supporting sleeve, each tubular membrane member having an inlet end and an outlet end, said inlet and outlet ends being embedded in annular blocks arranged about said cylindrical portion at a proximal and a distal end thereof, respectively, said blocks allowing fluid communication between said first channel means and one of said inlet and outlet ends of said plurality of tubular membrane members, and allowing fluid communication between said second channel means and the other of said inlet and outlet ends of said plurality of tubular membrane members.

2. The catheter according to claim 1, wherein said annular blocks and said plurality of tubular membrane members are arranged around said outer circumference of said supporting sleeve.

3. The catheter according to claim 1, wherein said annular blocks define a distribution chamber and a collection chamber, respectively, communicating with said first and second channels means, respectively.

4. The catheter according to claim 1, wherein said plurality of tubular membrane members are parallel to an axis of said cylindrical portion.

5. The catheter according to claim 1, wherein said plurality of tubular membrane members are inclined in relation to a plane through an axis of said cylindrical portion.

* * * * *